(12) United States Patent
McLaughlin et al.

(10) Patent No.: US 11,796,658 B2
(45) Date of Patent: *Oct. 24, 2023

(54) ATTENUATION ESTIMATION USING ULTRASOUND

(71) Applicant: Shenzhen Mindray Bio-Medical Electronics Co., Ltd., Shenzhen (CN)

(72) Inventors: Glen W. McLaughlin, San Carlos, CA (US); Albert Gee, Los Altos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/113,829

(22) Filed: Feb. 24, 2023

(65) Prior Publication Data

US 2023/0204743 A1 Jun. 29, 2023

Related U.S. Application Data

(63) Continuation of application No. 17/571,859, filed on Jan. 10, 2022, now Pat. No. 11,619,728, which is a
(Continued)

(51) Int. Cl.
*A61B 8/14* (2006.01)
*A61B 8/08* (2006.01)
(Continued)

(52) U.S. Cl.
CPC ............ *G01S 7/52036* (2013.01); *A61B 8/14* (2013.01); *A61B 8/5207* (2013.01); *A61B 8/5269* (2013.01); *G01S 7/5202* (2013.01); *G01S 15/8954* (2013.01); *G06T 7/0012* (2013.01); *G06T 2207/10132* (2013.01); *G06T 2207/20056* (2013.01)

(58) Field of Classification Search
None
See application file for complete search history.

(56) References Cited

U.S. PATENT DOCUMENTS 4,546,772 A 10/1985 Flax
5,361,767 A 11/1994 Yukov
(Continued)

OTHER PUBLICATIONS

Kim et al., "Attenuation Estimation using Spectral Cross-Correlation," IEEE Transactions on Ultrasonics, Ferroelectrics, and Frequency Control, vol. 54, No. 3, Mar. 2007.
(Continued)

*Primary Examiner* — Colin T. Sakamoto
(74) *Attorney, Agent, or Firm* — Kory D. Christensen

(57) ABSTRACT

Systems and methods for attenuation measuring using ultrasound. In various embodiments, echo data corresponding to a detection of echoes of one or more ultrasound signals transmitted into tissue are received. The echoes can be received from a range of depths of the tissue. Spectral measurements across the range of depths of the tissue are obtained using the echo data. Attenuation characteristics of the tissue across the range of depths of the tissue can be estimated using the spectral measurements across the range of depths of the tissue. Specifically, the attenuation characteristics of the tissue can be estimated using the spectral measurements and known spectral characteristics of the one or more ultrasound signals transmitted into the tissue.

20 Claims, 7 Drawing Sheets

Related U.S. Application Data continuation of application No. 16/242,287, filed on Jan. 8, 2019, now Pat. No. 11,275,159.

(51) Int. Cl.
    *G06T 7/00*     (2017.01)
    *G01S 7/52*     (2006.01)
    *G01S 15/89*     (2006.01)

(56) References Cited

U.S. PATENT DOCUMENTS

| | | |
|---|---|---|
| 2008/0221449 A1 | 9/2008 | Sato |
| 2010/0016719 A1 | 1/2010 | Freiburger et al. |
| 2012/0281497 A1 | 11/2012 | Noguchi |
| 2013/0011038 A1 | 1/2013 | Eda |
| 2014/0114189 A1 | 4/2014 | Kanayama et al. |
| 2014/0309531 A1 | 10/2014 | Eda |
| 2017/0258438 A1 | 9/2017 | Kanayama |
| 2019/0254634 A1 | 8/2019 | Honjo et al. |
| 2020/0049807 A1 | 2/2020 | Pekar et al. |
| 2020/0146656 A1 | 5/2020 | Gong et al. |
| 2021/0161505 A1 | 6/2021 | Kawashima |

OTHER PUBLICATIONS

Zhao et al., "Estimation of ultrasound attenuation and dispersion using short time Fourier transform," Ultrasonics 43 (2005) 375-381.

ATTENUATION ESTIMATION USING ULTRASOUND

CROSS-REFERENCE TO RELATED APPLICATIONS

This application is a continuation of U.S. application Ser. No. 17/571,859, filed Jan. 10, 2022, for ATTENUATION ESTIMATION USING ULTRASOUND, which is a continuation of U.S. application Ser. No. 16/242,287, filed Jan. 8, 2019, for ATTENUATION ESTIMATION USING ULTRASOUND, now U.S. Pat. No. 11,275,159, each of which is incorporated herein by reference.

TECHNICAL FIELD

This disclosure relates to ultrasound systems and methods and, in particular, to attenuation estimation across a range of depths of a tissue using ultrasound.

BACKGROUND OF THE INVENTION

Ultrasound imaging is widely used for examining a wide range of materials and objects across a wide array of different applications. Ultrasound imaging provides a fast and easy tool for analyzing materials and objects in a non-invasive manner. As a result, ultrasound imaging is especially common in the practice of medicine as an ailment diagnosis, treatment, and prevention tool. Specifically, because of its relatively non-invasive nature, low cost and fast response time, ultrasound imaging is widely used throughout the medical industry to diagnose and prevent ailments. Further, as ultrasound imaging is based on non-ionizing radiation, it does not carry the same risks as other diagnosis imaging tools, such as X-ray imaging or other types of imaging systems that use ionizing radiation.

In general, ultrasound imaging is accomplished by generating and directing ultrasonic sound waves into a material of interest, first in a transmit phase and subsequently in a receive phase. During the transmit phase, an ultrasonic signal is transmitted into a material of interest by applying continuous or pulsed electronic signals. During the receive phase, reflections generated by boundaries between dissimilar materials are received by receiving devices, such as transducers, and converted to electrical signals. Signals can then be processed to determine the locations of the echo sources. The resulting data can be used to display images of inside a material of interest, e.g. by displaying images using a display device, such as a monitor.

Ultrasound imaging can offer a wealth of clinical information. Specifically, ultrasound imaging can be used in abdominal ultrasound (to visualize abdominal tissues and organs), bone sonometry (to assess bone fragility), breast ultrasound (to visualize breast tissue), Doppler fetal heart rate monitors (to listen to a fetal heart beat), Doppler ultrasound (to visualize blood flow through a blood vessel, organs, or other structures), echocardiogram (to view a heart), fetal ultrasound (to view a fetus in pregnancy), ultrasound-guided biopsies (to collect a sample of tissue), ophthalmic ultrasound (to visualize ocular structures) and ultrasound-guided needle placement (in blood vessels or other tissues of interest). Ultrasound imaging has also been used in describing various disease states, such as diseases of the liver, breast, prostate, thyroid or other organs through single measurements of stiffness or shear wave velocity.

The attenuation of sound within tissue has been shown to vary based on tissue type as well as within a particular tissue type based on disease state. The ability to measure as well as track over time the attenuation properties of tissue within various organs has the potential to enable physicians to monitor the progression of a number of diseases. In addition, it enables the physician to measure the efficacy of the current therapy with the possibility to alleviate the need to acquire regular tissue biopsies. Using ultrasound to measure attenuation properties of tissue is advantageous due to the non-invasive nature of ultrasound. There therefore exist needs for systems and methods for measuring attenuation properties of tissue using ultrasound.

In order to achieve these measurements using ultrasound, a number of challenges exist. For example, limited bandwidth of transducers, variability across transducers, variability within a transducer, signal to noise ratio issues, and the like can lead to problems in measuring attenuation characteristics of tissue using ultrasound. Specifically, even though the transducer is a significant limitation of ultrasound system performance, the interactions of the sound waves with the tissue also results in reduced performance at depth due to a reduction of bandwidth from frequency dependent attenuation properties of tissue. However, attenuation characteristics of tissue across a range of depths of the tissue are the properties that are utilized by physicians to monitor progression of a number of diseases. There therefore exist needs for systems and methods that facilitate gathering attenuation characteristics of tissue across a range of depths of the tissue using ultrasound.

SUMMARY

According to various embodiments, a method for estimating attenuation characteristics of a tissue using ultrasound includes receiving echo data corresponding to a detection of echoes of one or more ultrasound signals transmitted into the tissue. The echoes can be received from a range of depths of the tissue. Spectral measurements across the range of depths of the tissue are obtained using the echo data. Attenuation characteristics of the tissue across the range of depths of the tissue can be estimated using the spectral measurements across the range of depths of the tissue. Specifically, the attenuation characteristics of the tissue can be estimated using the spectral measurements and known spectral characteristics of the one or more ultrasound signals transmitted into the tissue.

In certain embodiments, a system for estimating attenuation characteristics of a tissue using ultrasound includes an ultrasound transducer and a main processing console. The ultrasound transducer can be configured to transmit one or more ultrasound signals into the tissue. Additionally, the ultrasound transducer can be configured to detect echoes of the one or more ultrasound signals from the tissue across a range of depths of the tissue. The main processing console can be configured to receive echo data corresponding to a detection of the echoes of the one or more ultrasound signals transmitted into the tissue. Additionally, the main processing console can be configured to obtain spectral measurements across the range of depths of the tissue using the echo data. Subsequently, the main processing console can be configured to estimate attenuation characteristics of the tissue across the range of depths of the tissue using the spectral measurements across the range of depths of the tissue. Specifically, the main processing console can be configured to estimate the attenuation characteristics using the spectral measurements and known spectral characteristics of the one or more ultrasound signals transmitted into the tissue.

In various embodiments, a system for estimating attenuation characteristics of a tissue using ultrasound includes one or more processors and a computer-readable medium providing instructions accessible to the one or more processors to cause the one or more processors to perform operations including receiving echo data corresponding to a detection of echoes of one or more ultrasound signals transmitted into the tissue. The ultrasound signals can be received from a range of depths of the tissue. The instructions can further cause the one or more processors to obtain spectral measurements across the range of depths of the tissue using the echo data. Additionally, the instructions can cause the one or more processors to estimate attenuation characteristics of the tissue across the range of depths of the tissue using the spectral measurements across the range of depths of the tissue. Specifically, the instructions can cause the one or more processors to estimate the attenuation characteristics of the tissue using the spectral measurements and known spectral characteristics of the one or more ultrasound signals transmitted into the tissue.

DETAILED DESCRIPTION

Figure 1:
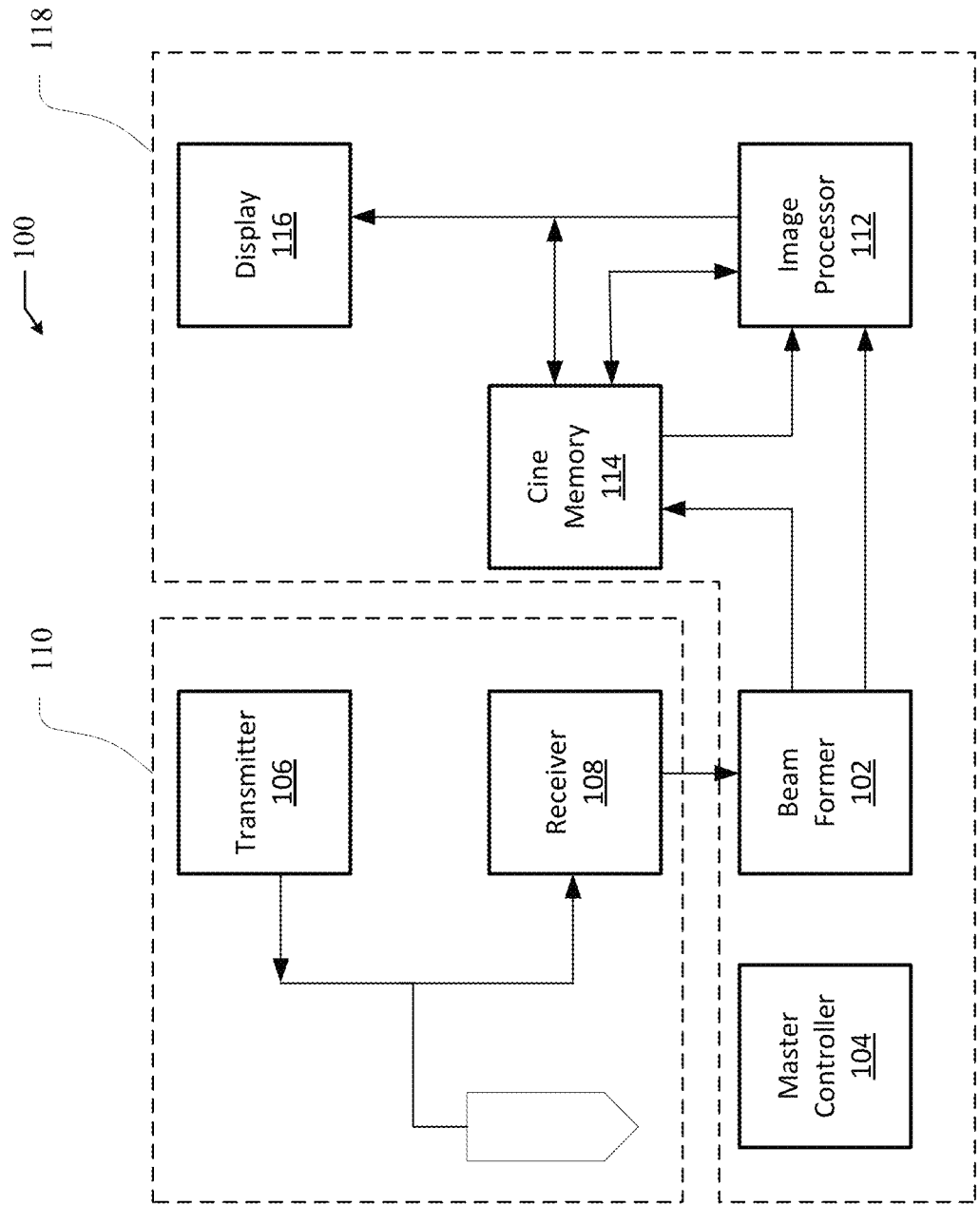
FIG. 1 illustrates an example of an ultrasound system.

Ultrasound transducers typically have a limited bandwidth and spectral response variability. Certain aspects of the transducer technology may be improved by using single crystal transducers, composite material transducers, capacitive micromachined ultrasonic transducers (CMUTs), piezoelectric micromachined ultrasonic transducers (PMUTs), or other improvements. As a result, there is a large variety of transducer types, each with different characteristics, performance, and shortcomings. However, there is still a great need for further improving ultrasound performance. Aspects of the subject technology provide for techniques and systems for measuring and shaping a spectral response, which results in an increased spectral bandwidth, e.g. for estimating attenuation characteristics of tissue. Furthermore, the subject technology provides a robust solution that can be applied to a wide variety of different transducer types and is compatible with other improvements in transducer technology.

The properties of a medium that the ultrasonic pulse travels through (e.g., the material of interest, such as organic tissue) may also affect the ultrasonic echo and distorts the resulting ultrasound image. For example, the medium may have an attenuation property and, in many cases, the attenuation property may be dependent on frequency. In other words, the medium may attenuate lower frequency ultrasonic signals (or the lower frequency portions of an ultrasonic signal) less than higher frequency ultrasonic signals (or the higher frequency portions of the ultrasonic signal). Furthermore, the rates at which ultrasonic signals are attenuated may vary based on the properties of the medium such as composition, density, layers, location of objects in the medium, etc. This may be especially true when the medium is organic tissue that may include a number of layers and/or components that may each have different characteristics. Furthermore, these layers and/or components may be dispersed throughout the tissue in a non-uniform manner. Aspects of the subject technology also provide for techniques and systems that compensate for the frequency dependent attenuation property of the medium and how the property affects attenuation at different depths.

Some aspects of the subject technology relate to processes, systems, and/or instructions stored on machine-readable medium that provide technical solutions to the above technical problems and others. For example, according to some embodiments, a transducer may be configured to transmit a pulse signal into a tissue. The pulse signal may be a broad spectrum long time coded calibration pulse, for example a chirp, (as opposed to an imaging pulse of short time but broad spectrum). Ultrasound echoes are generated based on reflections of the transmitted pulse signal on boundaries, objects, or other components in the tissue at various depths. These echoes may be received by the transducer and translated into echo data.

A set of fast Fourier transforms may be generated based on the received echo data. Each fast Fourier transform in the set may be associated with a particular depth value or range of depths. These depth values and ranges may be disjoint or, in some cases, overlap. A point estimates for a frequency dependent filtering coefficient of a spectral response for the each fast Fourier transform may also be generated. These point estimates may be used to form a line. In some cases, normalization steps may also be taken to smooth out the line. For example, a least means square fit process may be used.

A set of attenuation coefficients may be extracted from the line formed by the point estimates and these attenuation coefficients may be used to compensate for spectral response limitations of the transducer or for frequency dependent attenuation of the tissue of interest. For example, a second pulse signal may be transmitted into the tissue. This second pulse, in some cases, may be an imaging pulse that is shorter in time but still has a broad bandwidth than the initial calibration pulse used above. Echo data for the second pulse signal may be received and used, along with the set of attenuation coefficients, to generate an image of the tissue. For example, the attenuation coefficients may be used as inverse filters for the image data.

Although some embodiments may be discussed with respect to organic tissues, other mediums, materials, or objects of interest may similarly be used. Furthermore, although fast Fourier transforms are discussed with respect to some embodiments, other algorithms or signal conversion methods may also be used.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

FIG. 1 illustrates an example of an ultrasound system 100. The ultrasound system 100 shown in FIG. 1 is merely an example system and in various embodiments, the ultrasound system 100 can have less components or additional components. Specifically, the ultrasound system 100 can be an ultrasound system where the receive array focusing unit is referred to as a beam former 102, and image formation can be performed on a scanline-by-scanline basis. System control can be centered in the master controller 104, which accepts operator inputs through an operator interface and in turn controls the various subsystems. For each scan line, the transmitter 106 generates a radio-frequency (RF) excitation voltage pulse waveform and applies it with appropriate timing across the transmit aperture (defined by a sub-array of active elements) to generate a focused acoustic beam along the scan line. RF echoes received by the receive aperture 108 of the transducer 110 are amplified and filtered by the receiver 108, and then fed into the beam former 102, whose function is to perform dynamic receive focusing; i.e., to re-align the RF signals that originate from the same locations along various scan lines.

The image processor 112 can perform processing specific to active imaging mode(s) including 2D scan conversion that transforms the image data from an acoustic line grid to an X-Y pixel image for display. For Spectral Doppler mode, the image processor 112 can perform wall filtering followed by spectral analysis of Doppler-shifted signal samples using typically a sliding FFT-window. The image processor 112 can also generate the stereo audio signal output corresponding to forward and reverse flow signals. In cooperation with the master controller 104, the image processor 112 also can format images from two or more active imaging modes, including display annotation, graphics overlays and replay of cine loops and recorded timeline data.

The cine buffer 114 provides resident digital image storage for single image or multiple image loop review, and acts as a buffer for transfer of images to digital archival devices. On most systems, the video images at the end of the data processing path can be stored to the cine memory. In state-of-the-art systems, amplitude-detected, beam formed data may also be stored in cine memory 114. For spectral Doppler, wall-filtered, baseband Doppler I/Q data for a user-selected range gate can be stored in cine memory 114. Subsequently, the display 11 can display ultrasound images created by the image processor 112 and/or images using data stored in the cine memory 114.

The beam former 102, the master controller 104, the image processor, the cine memory 114, and the display can be included as part of a main processing console 118 of the ultrasound system 100. In various embodiments, the main processing console 118 can include more or fewer components or subsystems. The ultrasound transducer 110 can be incorporated in an apparatus that is separate from the main processing console 118, in a separate apparatus that is wired or wirelessly connected to the main processing console 118. This allows for easier manipulation of the ultrasound transducer 110 when performing specific ultrasound procedures on a patient.

As noted above, ultrasound systems operate on a limited bandwidth and/or have a limited reliable spectral response. The properties of the medium (e.g., the tissue) that the ultrasound system is directed at also distort ultrasound signals and, as a result, distort any resulting ultrasound image. Various embodiments of the subject technology are directed to improving these and other technical issues with ultrasound technology.

According to various embodiments, spectral measurements of the signals at various depths can be made and an estimate of the frequency dependent attenuation coefficient along with the passband response of the transducer can be obtained. Given that the attenuation coefficient of tissue will attenuate higher frequencies at a different rate (e.g., a faster rate) than lower frequencies the overall attenuation of the spectral response from the initial transmit spectral pulse is filtered into a lower and lower center frequency signal with narrower and narrower bandwidth as it propagates through the tissue. As the beams are formed the system can interrogate areas that represent primarily speckle so that a clean spectral estimate can be obtained at each depth.

According to some embodiments, the spectral estimates may be overlapping in depth to various extents. Several beam formed lines may also be used to get multiple spectral estimates and these estimates may be normalized or averaged to improve the overall signal to noise ratio (SNR) at each depth. Alternatively or additionally, the data may be averaged in place in a coherent manner to improve the overall SNR as well.

Once these spectral estimates are calculated at various depths, the known spectral characteristics of the transmit pulse along with the measured spectral estimates at depth can be used to estimate the transducer transfer function as well as the attenuation properties of the tissues with depth. This information can then be used to generate depth dependent inverse filters to compensate to some extent to the narrowing bandwidth and rate of frequency downshift of the waveform as it propagates through the tissue resulting in improving the system detail resolution performance characteristics at depth. The system may further be configured to measure the spectral SNR at the various depths and automatically determine and adjust how much gain should be applied to the signals at various depths and/or frequencies to ensure that it is primarily signal being compensated instead of just the noise.

According to some embodiments, the image processing of the incoming data from the reflected transmit pulse may include forming an image based on the one or more processing algorithms. These image forming algorithms may include beam formation, synthetic aperture techniques, or adaptive image formation techniques. This data could be obtained with either a unique transmit pulse that is used to obtain a more comprehensive spectral bandwidth of the system and tissue or with a standard imaging pulse. In some embodiments, a first estimate based on a unique pulse for large adjustment may be generated and a standard transmit pulse may be used to generate subsequent estimates to track changes for fine adjustments. Once the image has been formed, a gain compensation may be applied based on previous measurements. If there have been no previous measurements than an initial estimate of the gain compensation may be calculated without compensation.

A moving block fast Fourier transform (FFT) in the range direction may be performed in accordance with various embodiments. These transforms may be generated with overlapping ranges so that a smooth estimate of the parameters and compensation required can be made. In other embodiments, the FFTs may not have any overlap in range. Several FFTs along different range lines can be used to improve the overall estimate as their spectral profile can be averaged or the system can also coherently average several transmit/receive cycles in place to improve the overall SNR of the signal. The transducer and system parameter compensation may be applied to the signals in the spectral domain so that a slope calculation of the attenuation coefficient can be calculated. In some embodiments, once there is an estimate of the attenuation coefficient is estimated on a point basis, a moving average and/or least means squares fit can be applied to get a smoother varying estimate of the tissue attenuation.

According to various embodiments, a method for estimating attenuation characteristics of a tissue using ultrasound includes receiving echo data corresponding to a detection of echoes of one or more ultrasound signals transmitted into the tissue. The echoes can be received from a range of depths of the tissue. Spectral measurements across the range of depths of the tissue are obtained using the echo data. Attenuation characteristics of the tissue across the range of depths of the tissue can be estimated using the spectral measurements across the range of depths of the tissue. Specifically, the attenuation characteristics of the tissue can be estimated using the spectral measurements and known spectral characteristics of the one or more ultrasound signals transmitted into the tissue.

In certain embodiments, a system for estimating attenuation characteristics of a tissue using ultrasound includes an ultrasound transducer and a main processing console. The ultrasound transducer can be configured to transmit one or more ultrasound signals into the tissue. Additionally, the ultrasound transducer can be configured to detect echoes of the one or more ultrasound signals from the tissue across a range of depths of the tissue. The main processing console can be configured to receive echo data corresponding to a detection of the echoes of the one or more ultrasound signals transmitted into the tissue. Additionally, the main processing console can be configured to obtain spectral measurements across the range of depths of the tissue using the echo data. Subsequently, the main processing console can be configured to estimate attenuation characteristics of the tissue across the range of depths of the tissue using the spectral measurements across the range of depths of the tissue. Specifically, the main processing console can be configured to estimate the attenuation characteristics using the spectral measurements and known spectral characteristics of the one or more ultrasound signals transmitted into the tissue.

In various embodiments, a system for estimating attenuation characteristics of a tissue using ultrasound includes one or more processors and a computer-readable medium providing instructions accessible to the one or more processors to cause the one or more processors to perform operations including receiving echo data corresponding to a detection of echoes of one or more ultrasound signals transmitted into the tissue. The ultrasound signals can be received from a range of depths of the tissue. The instructions can further cause the one or more processors to obtain spectral measurements across the range of depths of the tissue using the echo data. Additionally, the instructions can cause the one or more processors to estimate attenuation characteristics of the tissue across the range of depths of the tissue using the spectral measurements across the range of depths of the tissue. Specifically, the instructions can cause the one or more processors to estimate the attenuation characteristics of the tissue using the spectral measurements and known spectral characteristics of the one or more ultrasound signals transmitted into the tissue.

Figure 2:
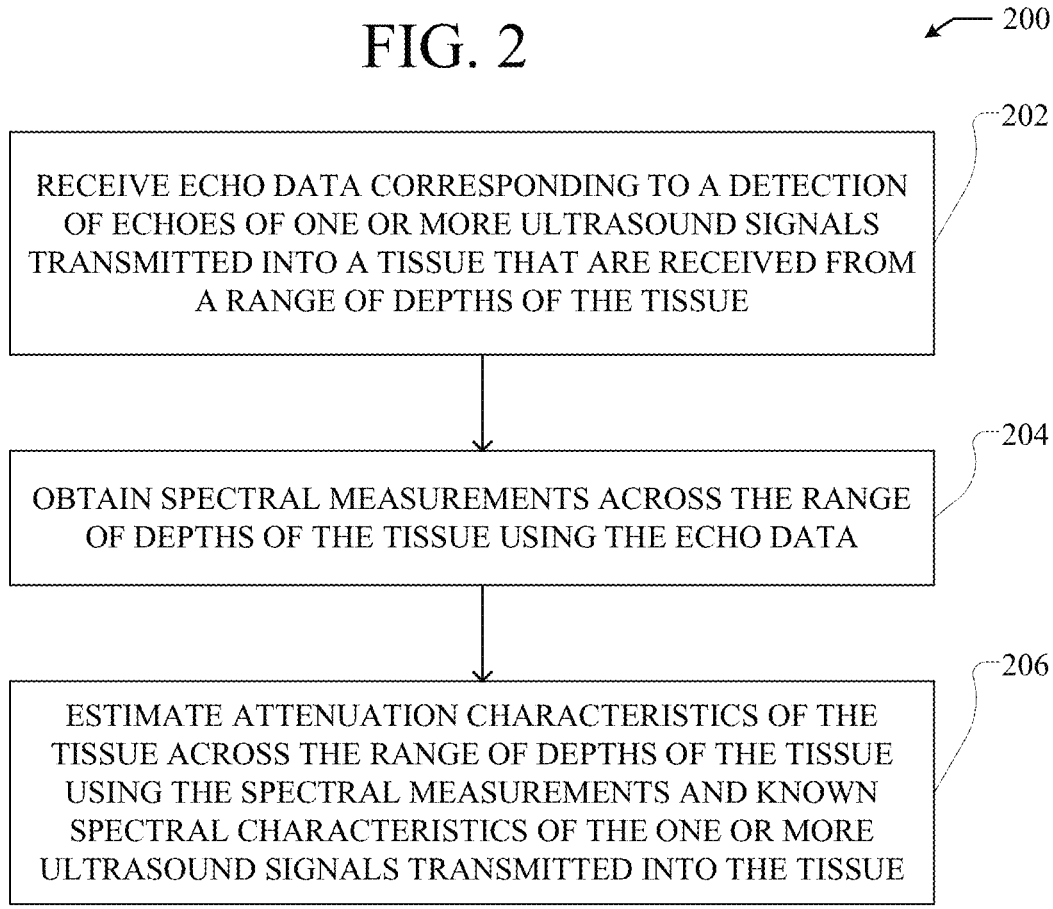
FIG. 2 is a flowchart illustrating an example method for estimating attenuation characteristics of a tissue using ultrasound.

FIG. 2 is a flowchart illustrating an example method 200 for estimating attenuation characteristics of a tissue using ultrasound. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200. For example, the method shown in FIG. 2 can be performed by an applicable ultrasound system, a transducer system, computing device, or similar system.

At operation 202, echo data corresponding to a detection of echoes of one or more ultrasound signals transmitted into the tissue is received. The echoes can be received from a range of depths of the tissue. As will be discussed in greater detail later, various operations can be performed to compensate for limitations of echo data received from tissue at ever increasing depths within the tissue. In turn, this can allow for estimation of attenuation characteristics of the tissue across a range of depths of the tissue, thereby leading to improved treatment and diagnosis of a patient. Specifically, doctors can more accurately diagnose and treat diseases when attenuation characteristics of the tissue are obtained across a range of depths of the tissue. The echo data can be generated by an applicable ultrasound system or component of an ultrasound system, such as the ultrasound system 100 shown in FIG. 1 and the transducer 110 and the main processing console 118 of the ultrasound system 100 shown in FIG. 1.

The echo data can be obtained with either a unique transmit pulse that is used to obtain a more comprehensive spectral bandwidth of the system and tissue when compared with a pulse used to perform standard ultrasound imaging. Specifically, the one or more ultrasound signals transmitted into the tissue can be formed by one or more broadband pulses. More specifically, the ultrasound signals transmitted into the tissue can be formed by broadband pulses having a pulse length greater than the pulse lengths of ultrasound signals used in performing ultrasound imaging. For example, a broad band spectral chirp pulse can be used to generate the ultrasound signals transmitted into the tissue. This can ensure that an increased/maximum signal to noise ratio is obtained with a broad spectral bandwidth, e.g. when compared to ultrasound pulses used in standard ultrasound imaging. In various embodiments, an image formed from the echo data is not actually displayed to a user. Accordingly, a long pulse and subsequent poor image characteristics as a result of the long pulse are not an issue. Additionally, the visible imaging problems created by the long pulse are not an issue as the attenuation from the skin line to the desired tissue typically is several millimeters away. As a result, the visible imaging problems created by the long pulse are satisfactory. While the ultrasound signals are described as being created from one or more broadband pulses, in various embodiments, the ultrasound signals used in measuring the attenuation characteristics of the tissue can be created using standard ultrasound imaging pulses.

At operation 204, spectral measurements across the range of depths of the tissue are obtained using the echo data. Spectral measurements can be obtained using applicable signal processing techniques, such as the signal/image processing techniques described herein. For example, and as will be discussed in greater detail later, the spectral measurements can be obtained based on the echo data using FFTs. Additionally, and as will be discussed in greater detail later, these spectral measurements can be used to estimate attenuation characteristics of the tissue across the range of depths of the tissue. For example, spectral measurements of the signals at various depths can be made and an estimate of the frequency dependent attenuation coefficient along with the passband response of the transducer can be obtained.

The echo data/spectral measurements can be filtered to identify spectral measurements across the range of depths of the tissue. Specifically, the echo data/spectral measurements can be filtered based on a depth of the one or more ultrasound signals within the tissue where the corresponding echo data is created. Subsequently, the spectral measurements can be obtained across, at least part of, the range of depths of the tissue using the filtered echo data. For example, echo data created by the ultrasound signals as the ultrasound signals travel deeper into the tissue can be filtered. Specifically, given that the attenuation coefficient of tissue will attenuate higher frequencies at a quicker rate than lower frequencies, the overall attenuation of the spectral response from the initial transmit, spectral measurements/corresponding echo data can be filtered into a lower and lower center frequency signal with narrower and narrower bandwidth as it propagates through the tissue, e.g. as the frequency decreases. In turn, the echo data can be filtered to decrease a lower central frequency of the echo data as the one or more ultrasound signals used to generate the echo data pass further and further into the tissue along the range of depths of the tissue, e.g. away from the skin line.

Further, spectral measurements can be obtained based on identification of areas in the range of depths of the tissue that are represented by speckle. Specifically, additional spectral measurements can be obtained, e.g. continuously obtained, for areas that represent primarily speckle/above a certain threshold amount of speckle. As a result, a clean spectral estimate can be obtained at a plurality of depths within the range of depths, even in areas where speckle exists. Subsequently, the spectral estimates of the areas represented primarily by speckle can also be used to estimate attenuation characteristics of the tissue across a range of depths of the tissue.

Additionally, the spectral measurements/estimates can overlap to some extent within the range of depths of the tissue. Specifically, several beamformed lines can be used to get multiple spectral estimates/measurements that overlap. In turn, the spectral estimates, e.g. overlapping estimates, can be averaged to improve the overall signal to noise ratio at each depth, e.g. when compared to spectral estimates that are not averaged. Specifically, averaging all or a portion of the spectral measurements can improve the overall signal to noise ratio across the entire range of depths of the tissue.

Further, the spectral estimates can be averaged in place as well as in a coherent manner, e.g. as discussed previously to improve the overall signal to noise ratio. Specifically, all or portions of the spectral estimates can be averaged, e.g. in place, regardless of whether the spectral estimates overlap or not, in order to improve the overall signal to noise ratio across the range of depths of the tissue. More specifically, spectral estimates can be averaged based on their corresponding depths within the tissue in order to improve the overall signal to noise ratio. For example, spectral estimates at greater depths, e.g. deeper from the skin in the tissue, can be averaged to improve the overall signal to noise ratio.

Additional processing can be applied to improve the overall signal to noise ratio, e.g. processes used for synthetic transmit focusing to improve the overall signal to noise ratio. Specifically, time varying inverse filters can only compensate/estimate the attenuation to a finite extent over time, because as the signals become increasingly attenuated, the desired signal at higher frequencies might be below the noise level. In order to counteract this problem, as discussed previously, the spectral measurements and/or echo data can be averaged in place to improve the SNR at depth. In turn, this can compensate for the problems of estimating attenuation at deeper levels and at higher bandwidths. Alternatively, the spectral signal to noise ratio can be measured over time. Subsequently, gains to apply at the various depths to compensate for the deficiencies in attenuation estimation can be identified, based on the measured signal to noise ratios. In turn the corresponding gains can be applied at the various depths/frequencies to ensure that a primarily signal is compensated/used for estimating attenuation instead of just noise.

As discussed previously, the spectral measurements can be identified using FFTs. Specifically, one or more image can be created using echo data. Subsequently, a set of FFTs can be generated based on the one or more images created using the echo data. Each FFT can be associated with a depth value in the range of depths of the tissue. In turn, a set of point estimates for a frequency dependent filtering coefficient, included as part of the spectral measurements can be generated across the range of depths of the tissue. Each frequency dependent filtering coefficient can correspond to one or more depths within the range of depths of the tissue. Subsequently, and as will be discussed in greater detail later, the set of point estimates can be used to estimate a set of attenuation coefficients, representing attenuation levels of the tissue/attenuation characteristics of the tissue, across the range of depths of the tissue.

Applicable ultrasound image processing techniques can be utilized to generate the one or more images from the echo data, e.g. for purposes of identifying the set of point estimates. Specifically, basic image processing can be applied to the echo data generated from the ultrasound signals to form an image. For example, standard beamformation, synthetic aperture techniques, or adaptive image formation techniques can be applied to the echo data to generate one or more images for purposes of generating the set of point estimates across the range of depths of the tissue.

In identifying the set of point estimates using FFTs, once the one or more images have been formed, a moving block FFT can be applied to the one or more images. Specifically, the moving block FFT can be applied in the range direction of the one or more images to identify the set of point of estimates. A range direction of the one or more images can correspond to a range of the depths within the tissue represented in the images. For example, the moving block FFT can first be applied to portions of the one or more images that correspond to regions in the tissue closest to the surface of the tissue. Then, the moving block FFT can be applied to portions of the one or more images representing ever decreasing depths of the tissue in the one or more images in order to generate the set of point estimates.

A range direction of the transforms is typically taken with overlap of the previous FFT so that a smooth estimate of the parameters and other applicable compensation(s) can be made. However, one or more moving block FFTs can be applied to different portions of the one or more images that do not overlap in range. For example, several moving block FFTs can be applied along different range lines to improve the overall estimates in the set of point estimates. Specifically, spectral profiles can be averaged and/or several transmit/receive cycles can be averaged in place to improve the overall SNR of the signal. In turn, this can improve the overall point estimates identified using FFTs.

At operation 206, attenuation characteristics of the tissue across the range of depths of the tissue can be estimated. Specifically, attenuation characteristics of the tissue can be measured using the spectral measurements and known spectral characteristics of the one or more ultrasound signal transmitted into the tissue. Spectral characteristics, e.g. known spectral characteristics, can include applicable characteristics describing ultrasound signals transmitted into a tissue. For example, spectral characteristics can include magnitudes of an ultrasound signal across a range of frequencies. Attenuation characteristics of the tissue across the range of depths of the tissue can include attenuation levels/ different attenuation levels at each depth across the range of depths of tissue. Specifically, once the spectral measurements/estimates are identified for various depths, at operation 204, then the known spectral characteristics of the transmit pulse/ultrasound signal(s) along with the measured spectral estimates at depth can be used to estimate the transducer transfer function as well as the attenuation properties of the tissues with depth. This information can then be used to estimate the attenuation of the tissue at various range depths as well as azimuthal locations. Subsequently, the estimated attenuation characteristics of the tissue can be presented to a user, e.g. for purposes of diagnosing or managing treatment of a disease.

In using FFTs to ultimately determine the attenuation characteristics of the tissue, a set of attenuation coefficients can be extracted based on the set of point estimates for the frequency dependent filtering coefficient. These attenuation coefficients can represent attenuation level/different attenuation levels across the range of depths of the tissue. The set of attenuation coefficients can be extracted based on the set of point estimates, as will be discussed in greater detail later, according to a slope of a line formed from the set of point estimates. Further, the set of attenuation coefficients can be extracted based on set of point estimates and the known spectral characteristics of the one or more ultrasound signals transmitted into the tissue. For example, the set of point estimates can be compared to the known spectral characteristics of the one or more ultrasound signals transmitted into the tissue to determine differences between the point estimates and the known spectral characteristics. These differences can correspond to different attenuation levels within the tissue across the range of depths of the tissue. Subsequently, the estimated attenuation coefficients can be presented to a user, e.g. for purposes of diagnosing or managing treatment of a disease.

The varying estimate of the attenuation levels across the range of depths of the tissue can be identified based on the estimated set of attenuation coefficients. Specifically, a moving average least means squares fit can be applied to the set of attenuation coefficients. to generate a smooth slowly varying estimate of the tissue attenuation across the range of depths of the tissue. Subsequently, the varying estimate of the attenuation levels across the range of depths of the tissue can be presented to a user, e.g. for purposes of diagnosing or managing treatment of a disease.

Figure 3:
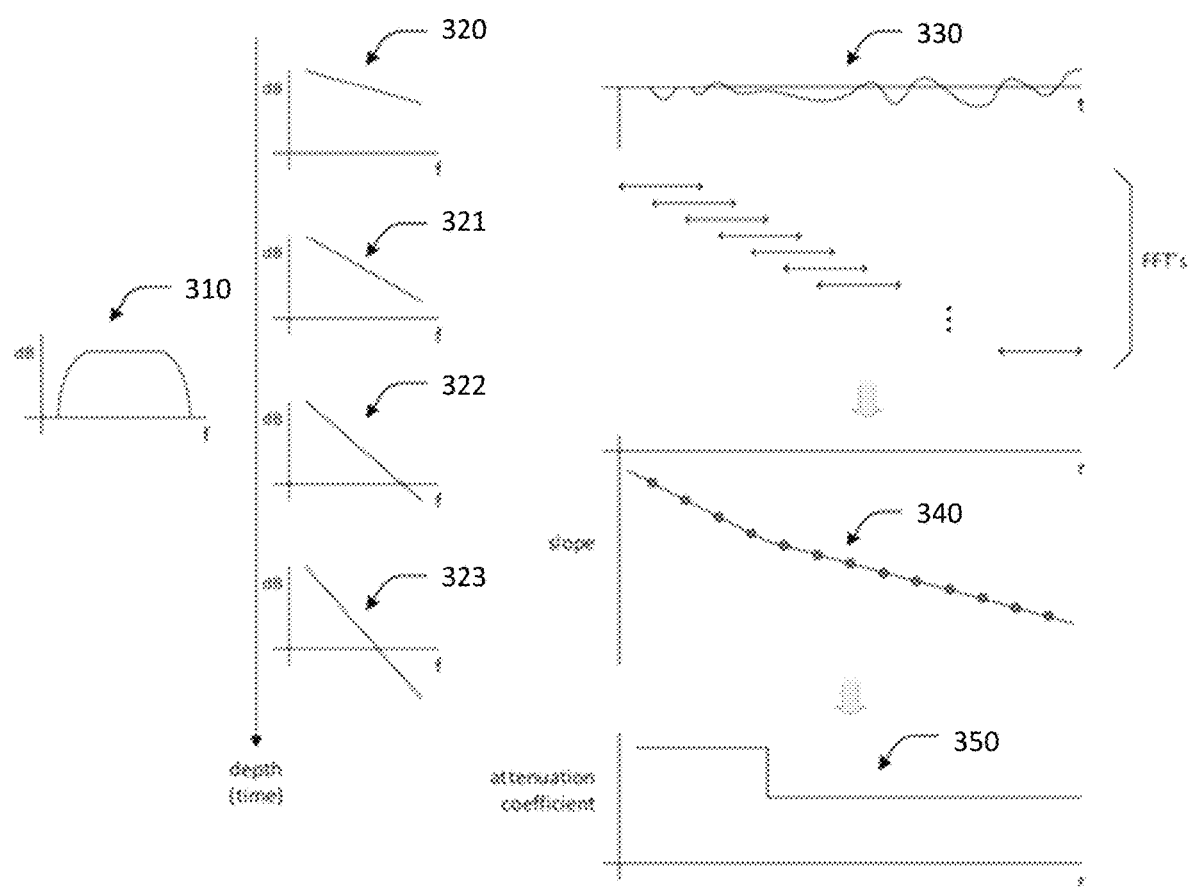
FIG. 3 is a diagram illustrating a process for generating a set of attenuation coefficients.

FIG. 3 is a diagram illustrating a process for generating a set of attenuation coefficients. In particular, FIG. 3 includes a graph 310 of a pulse signal. In particular, the graph 310 illustrates the amplitude (in decibels dB) and frequency of a pulse signal, such as a broad spectrum or broadband calibration pulse. According to various embodiments, a known broadband calibration pulse represented by graph 310 may be transmitted by the ultrasound system for a period of time into a tissue. Echoes caused by reflections and interactions between the broadband calibration pulse and the tissue at various depths may be received by the ultrasound system.

The calibration pulse may be filtered and distorted from interactions with both the transducer of the ultrasound system as well as the tissue. For example, in the near field, the distortion and filter effect may be primarily due to the transducer while, as the signal propagates through various depths, the spectral filtering of the higher frequencies increases. This is illustrated in graphs 320, 321, 322, and 323. More specifically, the graphs 320, 321, 322, and 323 help illustrate that different tissue depths (e.g., the time needed for ultrasound pulses to reach the tissue depth and echo), affect the spectral filtering of ultrasound pulses. The higher frequencies of the calibration pulse are filtered at a greater rate than the lower frequencies of the calibration pulse. Furthermore, as depth increases in graphs 320, 321, 322, and 323, this effect increases in prominence.

Based on the received signals from various scan lines at various depths (as illustrated in graphs 320, 321, 322, and 323), a set of overlapping in range fast Fourier transforms (FFTs) may be calculated. The set of FFTs is illustrated by graph 330. As illustrated by the graph 330, in some embodiments, the range of depths may overlap. In other embodiments, however, the depth values may not be ranges and/or may not overlap.

From this set of FFTs, point estimates of the slope of the line for the frequency dependent filtering coefficient of the spectral response can be calculated. These point estimates are illustrated by graph 340. From these point estimates a least means squares fit can be performed across a sub set of points to obtain an improved estimate of regional values of the slope of the line for the frequency dependent filtering of the spectral response. The regional slope of the frequency dependent filtering coefficient of the spectral response represents the corresponding attenuation coefficient. As a result, a set of attenuation coefficients may be extracted based on the set of point estimates. This is illustrated by graph 350, which shows 2 attenuation coefficients calculated for the portion of the line shown in graph 340. Conceptually, these attenuation coefficients may represent a change in slope in the line for the frequency dependent filtering coefficient in graph 340. These attenuation coefficients may be used to calculate a range dependent compensation filter to compensate for some of the spectral response reduction in the signal resulting in improved image performance from a detail resolution figure of merit measurement.

Various embodiments of the subject technology relate to obtaining an estimate of the depth varying spectral characteristics of the transmitted waveform. For example, a known transmit pulse spectrum may be transmitted and received at a range of depths of the tissue. The digitized signals may be processed in an image formation stage. A number of image formation techniques are possible to be used ranging from standard digital beam formation, synthetic aperture techniques, and adaptive image formation techniques. If there are already estimates for the gain compensation, those estimates may be applied. However, on a first iteration of the process (or if no estimate is available), the over depth gain compensation will most likely default to a standard value, for example an identity function.

After the gain compensation is done, the gain compensated signals can be used to form an image to be displayed to the systems user. Additionally, or alternatively, these same signals may also use to calculate a correction factor for the next iteration of the process. For example, the signals used for calculating the gain compensation and the correction factors may be used to calculate a set of spectral energy profiles (e.g., FFTs). These spectral energy profiles may be overlapping in range. These set of range based FFTs may be used to analyze the signals and determine if any additional transducer (XDR) or system compensation is required prior to calculating the spectral slope.

The spectral slope is calculated in range. In particular, estimates of the frequency dependent attenuation property of the material being imaged may be calculated. From these measurements an attenuation coefficient calculation is extracted at various depths. The attenuation coefficient at increasing depths is used to compensate the spectral properties of the image with increasing range provided there is sufficient signal to noise ratio at the higher frequencies.

Figure 4:
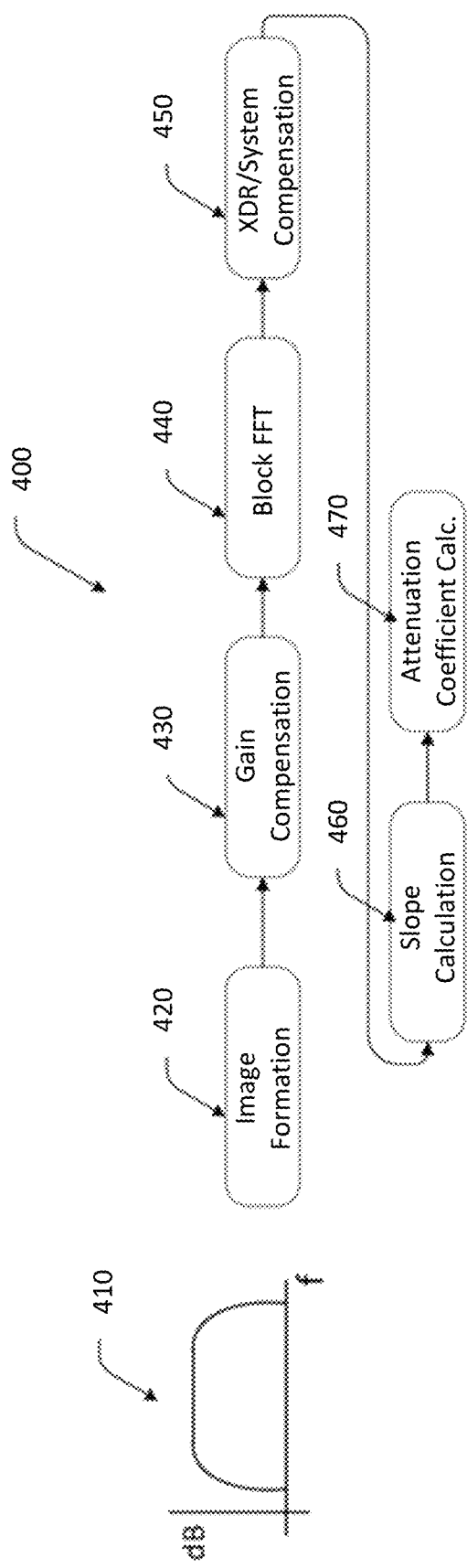
FIG. 4 shows a flowchart of a method for obtaining an estimate of depth varying spectral characteristics of a transmitted waveform.

FIG. 4 shows a flowchart of a method 400 for obtaining an estimate of depth varying spectral characteristics of a transmitted waveform. The method 400 shown in FIG. 4 can be used to estimate attenuation characteristics across a range of depths of a tissue according to the techniques described herein.

With reference to the method 400 shown in FIG. 4, a known transmit pulse spectrum 410 is transmitted and received at a range of depths from the tissue. Digitized signals received from the rage of depths from the tissue can then be processed in the image formation stage, at 420. A number of image formation techniques can be used to form one or more images at the image formation stage 420, such as standard digital beamformation, synthetic aperture techniques, and adaptive image formation techniques. At 430, gain compensation is applied. Specifically, an initial gain compensation is applied at 430 to compensate for the attenuation properties of the tissue. After gain compensation is applied at 430, a moving block FFT is applied, at 440, to the signals to generate a set of overlapping spectral energy profiles, e.g. a set of range-based FFTs. After the set of range-based FFT's are generated at 440, data compensation, e.g. additional transducer (XDR)/system compensation, can be applied at 450. Specifically, at 450, the signals can be analyzed to determine if any additional XDR or other applicable system compensation should be applied prior to calculating one or more spectral slop. At 460, a spectral slope is calculated within a range of depths. The spectral slope can be calculated, as discussed previously, by estimating frequency dependent attenuation properties of the tissue at various points within a field of view. At 470, one or more attenuation coefficients can be extracted at various depths and/or lateral positions within the tissue based on the spectral slope calculated at 460. Subsequently, the attenuation coefficient can be reported to the user as either or both a point estimate and a representation in a color coded regional map of attenuation within a specified field of view.

Figure 5:
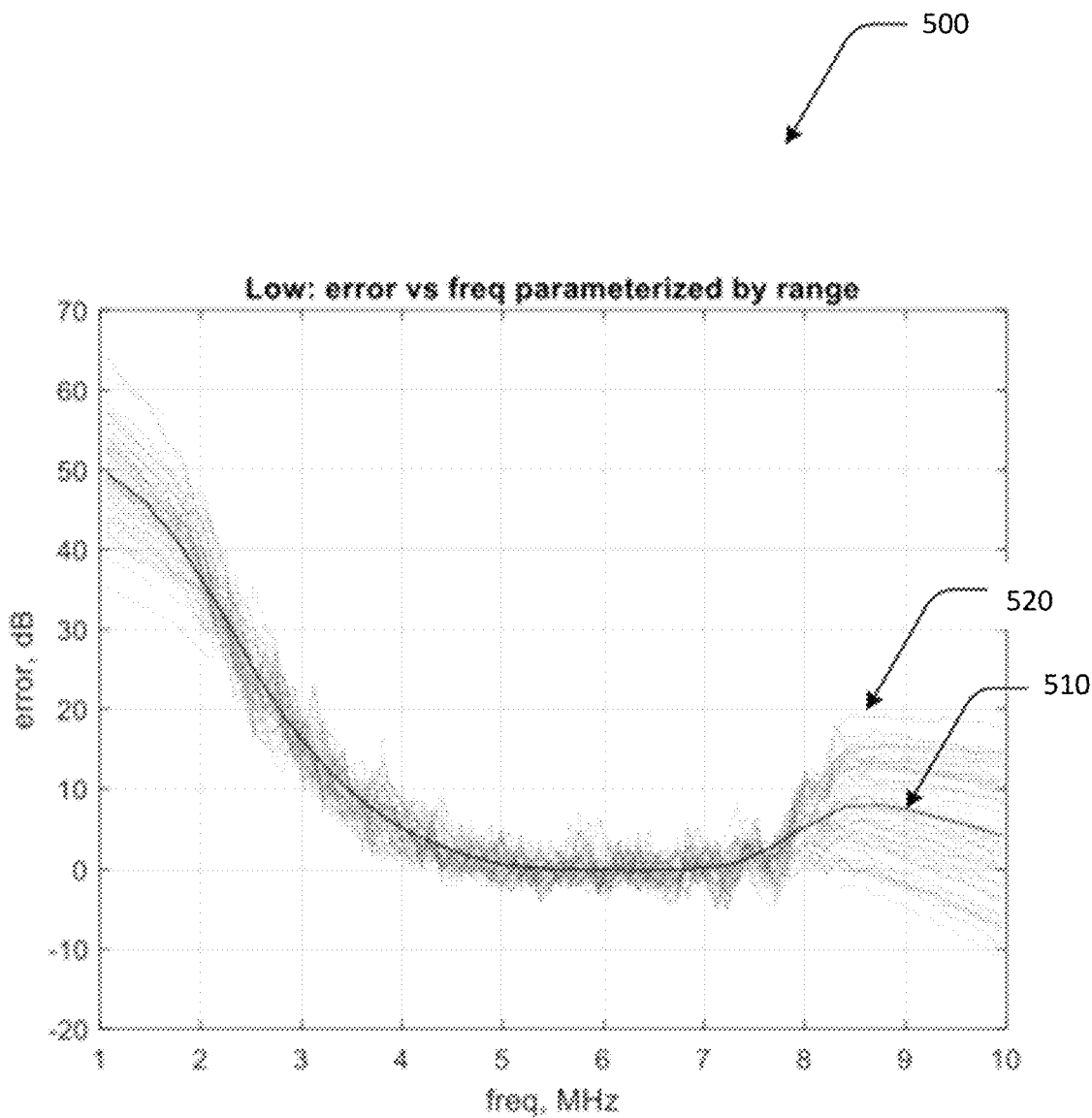
FIG. 5 is a graph illustrating a plot of the mean of the varying depth spectral estimates of a transducer, in accordance to various aspects of the subject technology.

FIG. 5 is a graph illustrating a plot 500 of the mean of the varying depth spectral estimates of a transducer, in accordance to various aspects of the subject technology. In particular, the mean estimate of the error of a flat spectral response of the transducer is shown by the solid line 510. It should be noted that the transducer used to make these measurements was a linear transducer that had a spectral frequency range from about 3 MHz to 8 MHz. The spectral estimates of the transducer response for varying depths are shown by the dotted lines 520. From frequencies of about 2 MHz to about 8 MHz the variance of the individual depth varying spectral responses 520 is fairly constant around the mean spectral response 510. Above and below these frequencies the variance diverges quickly. The reason for the tighter variance at the lower frequencies is that the overall signal to noise is was higher as the medium that the signals were transmitted into attenuates higher frequency signals more than lower frequency signals so the signal to noise ratio (SNR) of the signal decrease as the frequency increases. As a result, various aspects of the subject technology enable a wider range of frequencies of a transducer to be useful and increases the accuracy and image resolution across the transducer.

Figure 6:
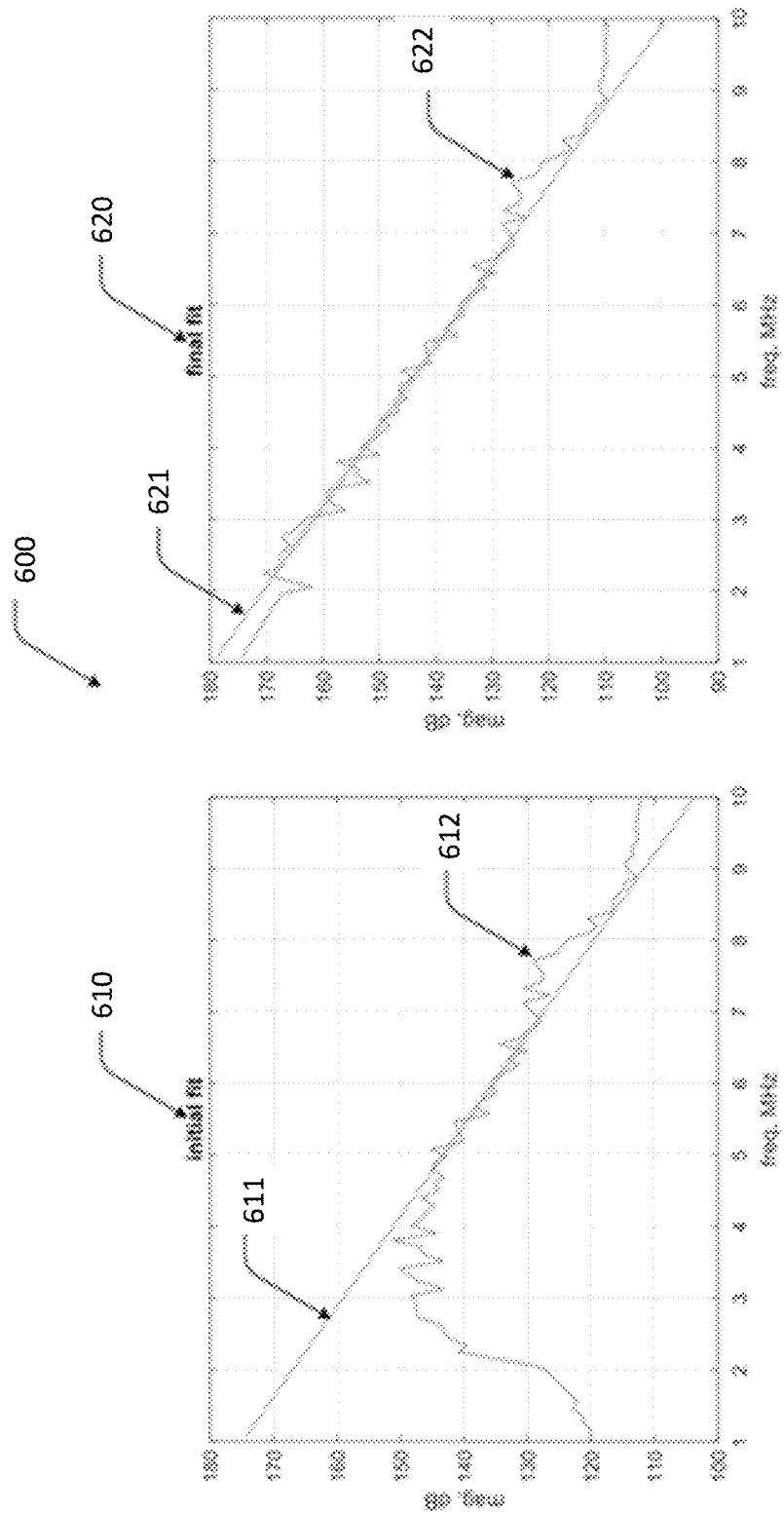
FIG. 6 is a set of graphs including a set of plots showing the spectral characteristics of a given depth from data uncompensated for transducer bandwidth limitation and one compensated.

FIG. 6 is a set of graphs 600 including a set of plots showing the spectral characteristics of a given depth from data uncompensated for transducer bandwidth limitation and one compensated. The uncompensated/raw spectral data in range is plotted in graph 610. The spectrum of this plot 612 of graph 610 shows a reasonably linear attenuation in dB with respect to frequency in the mid band of the transducer but the overall spectral fit to a line at the lower frequencies is minimal. A least mean squares fit line 611 using only the central portion of the spectrum for a given range of the uncompensated/raw spectral response is also shown in graph 610. As illustrated in graph 610, there is substantial roll off of the spectral signal at lower frequencies even though the overall SNR is good due to limitations of the transducer's frequency response characteristics.

A plot 622 of the compensated spectral data in range is plotted in graph 620. From this plot there is a significantly better linear attenuation in dB to frequency as compared to the uncompensated spectrum shown in graph 610. Also given the improved lower frequency spectral characteristics a least means squares fit line 621 is also improved. Comparing these two graphs 610 and 620 helps to illustrate that extracting the spectral response of the transducer and compensating for non-idealities in spectrum based on information contained within the spectral response of the transducer along a set of range samples is able to improve the overall systems spectral performance of various transducers and ultrasound systems.

Figure 7:
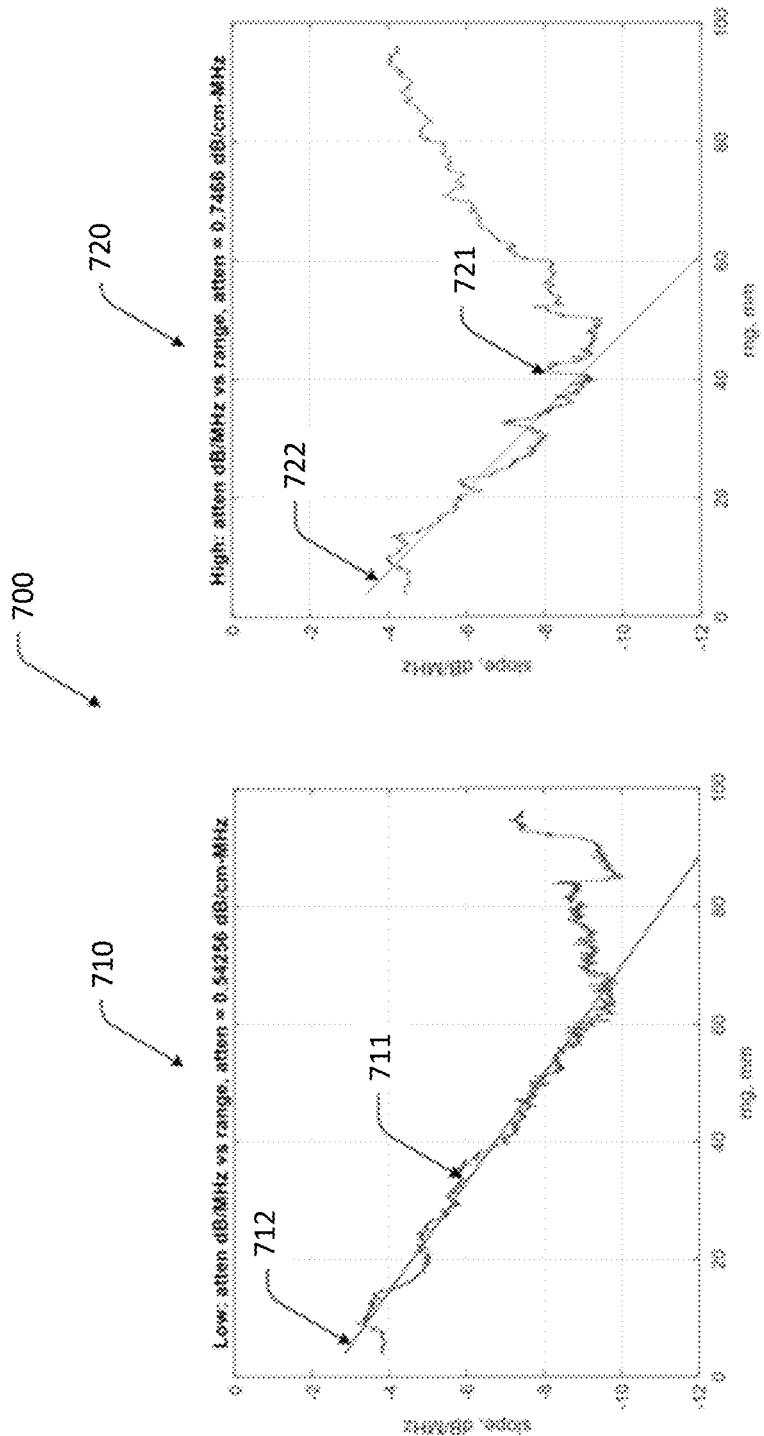
FIG. 7 shows example attenuation data estimates.

FIG. 7 shows example attenuation data estimates 700, e.g. attenuation characteristics, from a dual attenuation phantom (CIRS 040GSE) with a nominal attenuation of 0.5 dB/cm/MHz and 0.7 dB/cm/MHz.

On the left, a plot 710 of the phantom region of a nominal attenuation of 0.5 dB/cm/MHz is shown. The plot 710 includes an estimate of the attenuation of the signal spectral slope 711 of the signal at various depths. It can be seen that there is a reasonable consistent slope of the spectral slope from the surface to about 60 mm where the overall SNR of the signal becomes dominated by noise. As discussed previously, the depth at which noise becomes dominant can be increased by using a longer chirp pulse or averaging coherently several transmit receive cycles, as discussed previously. A least means square fit across this region, 712, shows that the slope of the least means square fit corresponds to an estimate of attenuation of about 0.5426 dB/cm/MHz or within the tolerance of the phantom manufacturer.

On the right, a plot 720 of the phantom region of a nominal attenuation of 0.7 dB/cm/MHz is shown. The plot 720 includes an estimate of the attenuation of the signal spectral slope 721 of the signal at various depths. It can be seen that there is a reasonable consistent slope of the spectral slope from the surface to about 40 mm where the overall SNR of the signal becomes dominated by noise. As discussed previously, the depth at which noise becomes dominant can be increased by using a longer chirp pulse or averaging coherently several transmit receive cycles. A least means square fit across this region, 722, shows that the slope of the least means square fit corresponds to an estimate of attenuation of about 0.7466 dB/cm/MHz or within the tolerance of the phantom manufacturer.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method for estimating attenuation characteristics of a tissue using ultrasound comprising:
    receiving echo data corresponding to a detection of echoes of one or more ultrasound signals transmitted into the tissue, wherein the echoes are received from a range of depths of the tissue;
    obtaining spectral measurements across the range of depths of the tissue using the echo data;
    estimating attenuation characteristics of the tissue across the range of depths of the tissue using the spectral measurements across the range of depths of the tissue and known spectral characteristics of the one or more ultrasound signals transmitted into the tissue;
    averaging the echo data generated by the one or more ultrasound signals based on a depth of the one or more ultrasound signals in the tissue where the echo data is created; and
    obtaining the spectral measurements across at least part of the range of depths of the tissue using the averaged echo data.

2. The method of claim 1, wherein the known spectral characteristics include magnitudes of the one or more ultrasound signals across a range of frequencies.

3. The method of claim 1, wherein the spectral measurements correspond to overlapping depth levels across the range of depths of the tissue, the method further comprising averaging the spectral measurements at the overlapping depth levels.

4. The method of claim 1, wherein the echo data is filtered to decrease a central frequency of the echo data as the one or more ultrasound signals used to generate the echo data pass further into the tissue along the range of depths of the tissue.

5. The method of claim 1, further comprising averaging the spectral measurements across at least a portion of the range of depths of the tissue to improve an overall signal to noise ratio across the range of depths of the tissue.

6. The method of claim 1, wherein the one or more ultrasound signals transmitted into the tissue are formed by one or more broadband pulses.

7. The method of claim 1, further comprising:
generating a set of fast Fourier transforms based on the echo data, wherein each fast Fourier transform in the set of fast Fourier transforms is associated with a depth value;
generating a set of point estimates for a frequency dependent filtering coefficient included as part of the spectral measurements across the range of depths of the tissue, where each point estimate in the set of point estimates corresponds to a fast Fourier transform in the set of fast Fourier transforms; and
extracting a set of attenuation coefficients based on the set of point estimates for the frequency dependent filtering coefficient, the set of attenuation coefficients representing one or more attenuation levels of the tissue across the range of depths of the tissue.

8. The method of claim 7, wherein the set of attenuation coefficients is extracted based on a slope of at least one line formed from the set of point estimates.

9. The method of claim 7, further comprising applying a least means square fit on the set of attenuation coefficients to generate a varying estimate of attenuation levels across the range of depths of the tissue.

10. The method of claim 7, further comprising:
generating one or more ultrasound images using the echo data; and
applying a moving block fast Fourier transform to the one or more ultrasound images to generate the set of fast Fourier transforms.

11. The method of claim 10, wherein the moving block fast Fourier transform is applied to the one or more ultrasound images is applied in a direction along the range of depths of the tissue.

12. The method of claim 10, wherein one or more fast Fourier transforms in the set of fast Fourier transforms are generated to have overlap with one or more previous fast Fourier transforms created by applying the moving block fast Fourier transform.

13. The method of claim 10, further comprising applying a plurality of moving block fast Fourier transforms to the one or more ultrasound images to generate the set of fast Fourier transforms, wherein the set of fast Fourier transforms includes a plurality of subsets of fast Fourier transforms and each subset of fast Fourier transforms corresponding to one of the plurality of moving block fast Fourier transforms used to create each subset of fast Fourier transforms.

14. The method of claim 13, further comprising averaging the set of attenuation coefficients based on the plurality of subsets of fast Fourier transforms to estimate the one or more attenuation levels of the tissue across the range of depths of the tissue.

15. The method of claim 7, wherein the set of attenuation coefficients is extracted based on the set of point estimates for the frequency dependent filtering coefficient included as part of the spectral measurements across the range of depths of the tissue and the known spectral characteristics of the one or more ultrasound signals transmitted into the tissue.

16. The method of claim 1, further comprising:
averaging the echo data generated by the one or more ultrasound signals based on a depth of the one or more ultrasound signals in the tissue where the echo data is created.

17. A system for estimating attenuation characteristics of a tissue using ultrasound comprising:
one or more processors; and
a computer-readable medium providing instructions accessible to the one or more processors to cause the one or more processors to perform operations comprising:
receiving echo data corresponding to a detection of echoes of one or more ultrasound signals transmitted into the tissue, wherein the echoes are received from a range of depths of the tissue;
obtaining spectral measurements across the range of depths of the tissue using the echo data;
estimating attenuation characteristics of the tissue across the range of depths of the tissue using the spectral measurements across the range of depths of the tissue and known spectral characteristics of the one or more ultrasound signals transmitted into the tissue;
averaging the echo data generated by the one or more ultrasound signals based on a depth of the one or more ultrasound signals in the tissue where the echo data is created; and
obtaining the spectral measurements across at least part of the range of depths of the tissue using the averaged echo data.

18. The system of claim 17, wherein the operations further comprise:
identifying areas in the range of depths of the tissue represented by speckle in the spectral measurements; and
continuing to obtain additional spectral measurements for the areas.

19. The system of claim 17, wherein the operations further comprise averaging the spectral measurements across at least a portion of the range of depths of the tissue to improve an overall signal to noise ratio across the range of depths of the tissue.

20. The system of claim 17, wherein the spectral measurements correspond to overlapping depth levels across the range of depths of the tissue, the operations further comprising averaging the spectral measurements at the overlapping depth levels.

* * * * *